(12) United States Patent
Montaser

(10) Patent No.: US 7,845,359 B2
(45) Date of Patent: Dec. 7, 2010

(54) ARTIFICIAL SMOKE CIGARETTE

(75) Inventor: Akbar Montaser, Potomac, MD (US)

(73) Assignees: Pierre Denain, Miami, FL (US); Richard Dolsey, Miami, FL (US)

(*) Notice: Subject to any disclaimer, the term of this patent is extended or adjusted under 35 U.S.C. 154(b) by 730 days.

(21) Appl. No.: 11/723,771

(22) Filed: Mar. 22, 2007

(65) Prior Publication Data

US 2008/0230052 A1 Sep. 25, 2008

(51) Int. Cl.
*A24F 47/00* (2006.01)

(52) U.S. Cl. ............ 131/273; 128/200.14; 128/200.16; 261/27; 438/689; 131/270

(58) Field of Classification Search ............ None
See application file for complete search history.

(56) References Cited

U.S. PATENT DOCUMENTS

| | | | |
|---|---|---|---|
| 726,037 A | 4/1903 | Ferré | |
| 2,445,476 A | 7/1948 | Folkman | |
| 2,764,154 A | 9/1956 | Murai | |
| 3,200,819 A | 8/1965 | Gilbert | |
| 3,365,102 A | 1/1968 | Castleberry | |
| 3,631,856 A | 1/1972 | Taylor | |
| 3,683,936 A | 8/1972 | O'Neil, Jr. | |
| 3,789,840 A | 2/1974 | Rosenblatt | |
| 4,184,496 A | 1/1980 | Adair | |
| 4,284,089 A | 8/1981 | Ray | |
| 4,393,884 A | 7/1983 | Jacobs | |
| 4,429,703 A | 2/1984 | Haber | |
| 4,765,347 A | 8/1988 | Sensabaugh, Jr. et al. | |
| 4,774,971 A | 10/1988 | Vieten | |
| 4,793,366 A | 12/1988 | Hill | |
| 4,813,437 A | 3/1989 | Ray | |
| 4,892,109 A | 1/1990 | Strubel | |
| 4,911,181 A | 3/1990 | Vromen et al. | |
| 4,920,989 A | 5/1990 | Rose et al. | |
| 4,945,929 A | 8/1990 | Egilmex | |
| 4,953,572 A | 9/1990 | Rose et al. | |
| 4,995,407 A | 2/1991 | Kossiakoff et al. | |
| 5,060,671 A | 10/1991 | Counts et al. | |
| 5,284,163 A | 2/1994 | Knudsen | |
| 5,293,883 A | 3/1994 | Edwards | |
| 6,041,789 A | 3/2000 | Bankert et al. | |
| 6,443,146 B1 * | 9/2002 | Voges | 128/200.14 |
| 2001/0023130 A1 * | 9/2001 | Gilton et al. | 438/689 |
| 2002/0059939 A1 | 5/2002 | Fox | |
| 2002/0179101 A1 | 12/2002 | Chavez | |
| 2003/0111088 A1 | 6/2003 | Fox | |
| 2005/0016553 A1 | 1/2005 | Iannuzzi | |
| 2005/0236006 A1 | 10/2005 | Cowan | |

FOREIGN PATENT DOCUMENTS

WO    WO 2004/080216 A1    9/2004

* cited by examiner

*Primary Examiner*—Philip C Tucker
*Assistant Examiner*—Phu H Nguyen
(74) *Attorney, Agent, or Firm*—Patton Boggs LLP

(57) ABSTRACT

An artificial cigarette, inhaler or other nebulizer device may include a housing, an air passage into the housing, a fog generator chamber within the housing connected to the air passage, a liquid source connected to the fog generating chamber, and a fog generator within the fog generating chamber for receiving liquid from the liquid source and creating an aerosol. The fog generator may be an ultrasonic nebulizer and/or a pneumatic nebulizer.

21 Claims, 8 Drawing Sheets

ARTIFICIAL SMOKE CIGARETTE

FIELD OF THE INVENTION

The invention relates generally to methods and apparatus for inhaling aerosol droplets. The invention may also relate generally to methods and apparatus to simulate the appearance, taste and other characteristics of a traditional cigarette and, more particularly, to apparatus and related methods for an artificial cigarette with reduced adverse health side effects.

BACKGROUND OF THE INVENTION

Cigarette smoking first became a mass "epidemic" in the United States, United Kingdom and other more wealthy countries in the early 20th century after the launch of inexpensive, mass produced cigarettes. As shown in FIG. 1, this "epidemic" usually develops in four stages. Often, the uptake and ensuing adverse effects of smoking occur earlier and to a greater degree among men. The four stages of a smoking "epidemic" for men are generally: (1) an initial slow rise in smoking prevalence, (2) a more rapid rise in smoking prevalence with an increase in the number of smoking related deaths, (3) a decrease in smoking prevalence with a more rapidly increasing number of smoking related deaths, and (4) a continued decline in smoking prevalence with a parallel trend in smoking related diseases. Generally, a decline in smoking prevalence is trailed approximately two to three decades later by the parallel trend in smoking related diseases.

The number of smokers worldwide is gradually rising. Presently, an average of 35% of the worldwide population between ages 15 to 64 smokes. A rapid increase in smoking prevalence throughout the developing world is one of the key threats to present and future world health. For most smokers quitting smoking is the single most important act to improve their health. Encouraging smoking cessation is one of the most effective and cost effective actions that health professionals can suggest for improving health and prolonging patients' lives. Based on data from the Center for Disease Control and Prevention (CDC), 24.7% of adults in the United States were smokers in 1997. Smoking in turn has lead to nearly 430,000 preventable deaths. Cigarette smoking is the single largest avoidable cause of death and disability in developed countries. One of the national health objectives for the United States in 2000 was to reduce the prevalence of cigarette smoking among adults to less than 15%. Roughly 20.9% of adults in the United States were current cigarette smokers in 2005. This figure reveals that the 8-year decline in smoking prevalence among adults in the United States has not met the 2000 objectives. In fact, the decline in smoking prevalence may be stalling when considering increases in population. As seen in FIG. 2, the smoking movement in United Kingdom depicts a similar trend. An estimated 2.3% of adults in the United States in 2005 used smokeless tobacco. Additionally, 42.5% of current cigarette smokers did quit smoking for at least one day in the preceding 12 months in an attempt to quit smoking permanently.

For most countries, the situation is worse. The 1995 smoking prevalence data from studies in 139 countries show 29% of persons aged 15 years or older were regular smokers globally in 1995. Four fifths of the world's 1.1 billion smokers in 1995 resided in low- or middle-income countries, with East Asian countries constituting an excessively high percentage (38%) of the world's smokers. Males comprised four fifths of all smokers. FIG. 3 shows cigarette smoking by deprivation level in the United Kingdom. Forthcoming decades will see rapid increases in tobacco-related deaths in low- and middle-income regions, even in rich countries such as the United Kingdom.

Half of the smokers will die prematurely of a disease caused by their smoking, losing an average of eight years of life. These figures are based upon an estimated 4 million deaths per year from tobacco in 1999, and these figures are anticipated to climb to an estimated 10 million deaths per year from tobacco by the 2030's. On the basis of the 2002 smoking trends, tobacco-attributable disease will kill about 500 million people over the next five decades.

Current evidence clearly indicates that smoking cessation reduces the risk of death from tobacco-related diseases. For example, lung cancer, which is particularly deadly with 85% of the patients dying within five years of their diagnosis, is almost entirely preventable. People who quit smoking reduce their risk of dying over the next 15 years by 50% compared with those who still smoke. For example, among physicians in the United Kingdom those who stopped smoking before the inception of major disease avoided most of the excess peril of smoking. The advantages of quitting were prevalent in those who suspended early (between ages 35 and 44) but were still momentous in those who quit later (between ages 45 and 54 years). While much of this high mortality can be reduced if smokers discontinue smoking, quitting is unusual, particularly in low- and middle-income countries. For instance, the occurrence of childhood mortality, smoking, and tuberculosis in India is three times higher among the lowest income or education groups than among the highest. One simple solution to reduce the mortality rate is increasing cigarette tax to four-fifths of the retail price which would roughly double the price of cigarettes in low-income countries. This practice, along with complete bans on advertising and promotion, could quadruple smoking cessation rates to nearly 30%. Based on recent data the cited combined strategies would ultimately prevent somewhere between 60 to 120 million deaths between 2002 and 2050.

The impact of smoking on longevity is well documented, is dependent on the levels of exposure, and is greater among younger smokers. FIG. 4 shows the numbers and relative risk of death by cause due to smoking in the United Kingdom. The data in FIG. 4 shows the strongest cause-specific links with respiratory cancers and chronic obstructive pulmonary ailments; in numeric terms, the greatest health impacts of smoking are on respiratory and cardiovascular diseases. Smokers are also at greater danger of several non-fatal diseases, such as osteoporosis, periodontal disease, impotence, male childlessness, and cataracts.

Cigarette smoking is also likely to have toxic effects on the retina which can cause severe and irreversible vision loss with increased risk of 2-3 fold in current smokers compared with never-smokers. Smoking in pregnancy is allied with enhanced rates of fetal and prenatal loss and diminished birth weight. Passive smoking after birth is associated with bed death and respiratory disease in childhood and lung cancer, heart disease, and stroke in adults. It is now well established in clinical practice that the toxic constituents of cigarette smoke, particularly nicotine, carbon monoxide, and hydrogen cyanide, also undermine expeditious wound repair. This is because nicotine reduces nutritional blood flow to the skin. Carbon monoxide diminishes oxygen transport and metabolism, whereas hydrogen cyanide hinders the enzyme systems necessary for oxidative metabolism and oxygen transport at the cellular level. Approximately 11 minutes of life expectancy is lost from smoking a single cigarette.

Another major disorder is alcoholism, which poses a substantial health problem, costing approximately $165 billion per year just in the United States. In addition to the above health concerns, cigarette smoking is more common in alcoholics than in the general population, with as many as 80-95% of alcoholics being smokers. This high percentage of co-morbidity reflects overlapping biochemical mechanisms of nicotine and alcohol in the central nervous system, which seems to result in even greater addiction to both drugs. Needs exist for new products that offer a combination therapy for smoking and alcoholism.

The adverse health effects and deadly diseases caused by smoking are attributed to nicotine and cigarette smoke. Nicotine is the addictive agent that prevents smokers from quitting, and is possibly responsible for more undesirable health consequences than any other single compound. The conversion of nicotine, the most common alkaloid found in tobacco, by the body into chemicals such as amino ketones have been shown to cause various diseases. Cigarette smoke contains more than 4,000 chemical compounds including at least 60 carcinogens. The carcinogenic compounds in cigarette smoke can be divided into four types: 1) nitrosamines, generally considered as the most deadly cancer-causing agents in tobacco smoke; 2) aldehydes, produced by the burning of sugars and cellulose in tobacco; 3) polycyclic aromatic hydrocarbons (PAHs), which form in the cigarette behind the burning tip; and 4) traces of heavy metals present in tobacco as a result of fertilizers used on the plant.

Historically, the development of a safer cigarette has been hampered for three reasons. First, and most importantly, removal of the toxins out of smoke has been a technological challenge because the taste and smoking sensations has not been satisfactorily preserved. Second, the cigarette companies were initially reluctant, due to legal problems, to admit that their "existing" products were dangerous. Third, the profound distrust of the cigarette companies by anti-tobacco activists and health officials played an obstructionist role even when significant progress was being made in a given area. For example, the consumer demand for a safer cigarette led the cigarette makers to gradually reduce the average tar level of cigarettes from 46.1 mg of tar per cigarette to 12.0 mg from 1944 to 1994. Lower-tar cigarettes appear to reduce the lung cancer risks of smoking, but not many of the other hazards. As discussed below, this and similar shortcomings led the anti-tobacco activists, health officials, and Food and Drug Administration to focus, for example, on eliminating smoking behavior and discouraging the promotion of safer cigarettes, rather than fostering additional technological innovations to radically promote cigarette safety, similar to safety improvements in motor vehicles. Collectively, such issues dissuaded the cigarette makers to aggressively conduct more research towards the development and marketing of safer cigarette.

The filter cigarettes introduced in the 1950's were the first attempt by the cigarette companies to introduce a safer cigarette through reduction of the tar level. Sales of filter cigarettes surged from less than 1 percent of the market in 1950 to 87 percent in 1975, but little evidence was presented to suggest that filter cigarettes were any healthier than regular cigarettes. Based on a 2006 court ruling even the alleged light or ultra-light cigarettes used today are marketing ploys and are not better than the full-strength smokes because, for example, the smokers compensate for the lower nicotine levels from the low-tar cigarettes by puffing more often or through deeper inhalation.

To remove the toxins from a conventional cigarette without altering the taste or smoking experience, cigarette makers initiated extensive research in four areas during 1960s: 1) selective filtration of the most noxious substances in cigarette smoke, such as carbon monoxide; 2) the removal or lowering of nicotine and the four types of carcinogenic compounds cited above; 3) the development of synthetic tobacco and tobacco substitutes; and 4) increasing nicotine levels in low-tar cigarettes to prevent compensation by smokers for a loss of nicotine. Unfortunately, lowering the levels of one or two hazardous compounds either raised the levels of other unsafe compounds, made the cigarette "taste" unacceptable to the smokers, or raised concerns by health groups and the cigarette companies. For example, a new cigarette, FACT, introduced by Brown & Williamson in 1975, was withdrawn from the market after two years though it could selectively eliminate certain compounds, including cyanide, from cigarette smoke. Similarly, a cigarette developed in the "XA project" in the 1970's by Liggett Group, Inc. contained catalysts such as palladium blended with tobacco to destroy PAH's formed behind the cigarette's burning tip, but this project was terminated due to pressure by other cigarette makers because of a direct or implied admission that all other cigarettes were hazardous. In addition, due to opposition by health group, the cigarettes introduced in 1977 by British firms Imperial, Gallaher, and Rothmans were removed from the market after a few months although tobacco was replaced with less toxic substitutes, including ingredients made from wood pulp. These and similar situations caused other cigarette companies to begin reducing their efforts by early 1980's to develop a safer cigarette, and even hiding some of the results of prior research, as illustrated in the 1994 lawsuit by the State of Minnesota against the tobacco industry. A former Philip Morris researcher testified in 1998 that the company abandoned promising research to eliminate cadmium, a lung irritant, from tobacco to protect itself against additional liability.

Beginning mid-1980's, cigarette makers began to market high-tech cigarettes that were supposedly safer, or more socially acceptable with less visible side stream smoke or less odor. A recent study reveals that 28 such projects had been underway since 1970's at R J Reynolds, Philip Morris, British American Tobacco, and Lorillard tobacco companies. Despite these efforts and heavy investment on research, almost every product developed was unacceptable in actual product tests or test markets. Smokers required complete elimination of secondhand smoke to please non-smokers, they were usually reluctant to forfeit their own smoking pleasure for the benefit of others, and favored smoke-free environments to cigarettes that generated less secondhand smoke. For example, the high-tech cigarette called PREMIER introduced in 1988 by R J Reynolds after an investment of nearly $800 million dollars in research was almost smokeless, reducing the cancer-causing compounds inhaled through heating aluminum capsules having tobacco pellets. This cigarette, perhaps the greatest technological innovation affecting cigarettes, was removed from the market in 1989 because it required its own instruction booklet to light it, did not taste like regular cigarettes to some smokers, consumers did not get used it, and the cigarette faced regulation by FDA as a drug. The PREMIER brand eventually evolved into the ECLIPSE smokeless cigarette in 1994, which was similar to a regular cigarette, but claiming reduction in secondhand smoke by 85 to 90 percent to be more socially acceptable. It differed from a regular cigarette in that the nicotine was extracted by heating the tobacco with air passed through a burning charcoal heat source at lower temperature. Because ECLIPSE has simpler smoke chemistry, consisting of 80% glycerol and water, it contained fewer toxic components resulting in reduced mutagenicity and cytotoxicity in in-vitro tests and fewer DNA adducts. In more recent studies, however, public health officials showed that ECLIPSE appears to be at least as toxic as some commercially available cigarette brands, and produces more carbon monoxide and higher levels of other carcinogenic PAH's compared to the "light" brands such as NOW and CARLTON. Importantly, when glycerin is burned, it is known to be carcinogenic.

As to nicotine, which is mainly connected to the difficulty of quitting smoking, Philip Morris made an important contribution. The company had noted that older, female, low-tar cigarette smokers are generally most interested in the nicotine-free cigarette. A supercritical carbon dioxide process was used to remove nicotine from tobacco, leading to a "97% nicotine-free" cigarette under the brand names NEXT and MERIT FREE, which were test marketed in 1989. Granted, these cigarettes were actually designed to deter smokers from quitting, and tobacco critics claimed that NEXT had higher tar levels than some cigarettes. However, the products promoted further technological developments towards safer cigarettes. Anti-smoking groups petitioned the FDA to designate nicotine as a drug and to begin a broader range of regulatory actions against cigarettes. Although the idea of the reduced-nicotine products appealed to smokers, Philip Morris never launched NEXT after poor consumer reactions to the actual cigarette. Several versions of MERIT are currently available, with one version, under the packaging name ULTIMATE KING FILTER BOX, having very low levels of tar (1 mg) and nicotine (01.mg).

Another high-tech cigarette developed by Philip Morris in 1988 is ACCORD, which had to be used with a special kit having a puff-activated electronic lighter and a battery charger. To smoke, most of the cigarette was inserted into a tube-shaped lighter equipped with sensors that controlled the temperature of the heated tobacco for reducing carcinogenic compound production and side smoke. As the smoker sucked on the lighter, a microchip sensed the puff to send a burst of heat to the tobacco. The process gave the smoker one drag, a display offered the number of remaining puffs before recharging the batteries, typically required after using the cigarette pack The cigarette was test marketed only in Richmond, Va., and is no longer available partly because the lighter was bulky and cumbersome to use, the smoker had to learn a completely new smoking practice, and the cigarette still produced carcinogenic products. The tar (3 mg) and nicotine (0.2 mg) of ACCORD were higher than some versions of MERIT.

Another promising step towards safer cigarettes involved development of nitrosamine-free cigarettes as nitrosamines are cancer causing compounds. A special tobacco curing process allowed cigarette makers such as Brown & Williamson and RJ Reynolds to drastically reduce the formation of tobacco-specific nitrosamines in the tobacco used in special brands. One must note, however, that cigarettes without nitrosamines produce other carcinogens.

The cigarette industry has been unable to offer a safe cigarette despite heavy investment, and as far as the consumer is concerned the safest cigarette is no cigarette at all, which is not a realist goal. Even though the public has come to recognize smoking hazards, in many cases they have been reluctant or unable to drop the habit because of addiction to nicotine or due to deriving pleasure from holding a cigarette and drawing air through the cigarette via the hand-to mouth action.

Various techniques have been advanced on controlled nicotine delivery to aid smoking cessation. The five major pharmacotherapies are: 1) nicotine gums; 2) nicotine patches; 3) nicotine nasal sprays; 4) nicotine inhalers; and 5) sustained-release bupropion hydrochloride, a non-nicotine medication. Other examples of smoking cessation aids include: 1) nicotine nose drops; 2) nicotine lozenges; 3) compositions comprising nicotine metabolites; 4) drinkable nicotine solutions; and 5) smoke-free cigarettes.

A significant effort has been underway over the development of smokeless cigarettes.

One focus has been based on treatment to help individuals to give up the smoking habits via physical devices. For example, U.S. Pat. No. 2,445,476 offers a mixture of volatile agents and essential oils (such as 50% menthol, 20% peppermint oil, 10% eucalyptus oil, 10% spearmint oil, and 10% wintergreen oil as a substitute for an all-tobacco cigarette. This mixture is adsorbed on the cigarette fillers such as wool yarn and cotton rolls, but inhalation of the volatile mixtu requires no cigarette lighting. Similarly, the sucking pipe in U.S. Pat. No. 2,764,154 provides enclosures suitable for atomization/vaporization of tobacco fragrance dissolved in drining alcohol, thus allowing inhalation by the user at non-smoking places such as theaters, buses, and hospitals. U.S. Pat. No. 3,365,102 shows a simulated cigarette constructed to contain and dispense through sipping a limited volume of liquid beverages such as flavored syrups or liquid, medical preparations, tobacco extracts, or other potable liquid suitable to the individual taste. In U.S. Pat. No. 3,683,936 the industrially accepted process of micro-encapsulation is utilized to implant a simulated smoking device with the flavor and aroma of tobacco smoke for passage into the mouth of the user without lighting the cigarette to create smoke. U.S. Pat. No. 3,789,840 illustrates a device that offers a chemical substance such as a lozenge to suppress the craving for smoking and also to satisfy the psychological requirement associated with giving up smoking through the use of simulated ash which can be luminous under the control of the smoker. U.S. Pat. No. 3,200,819 describes a smokeless non-tobacco cigarette in which the burning tobacco and paper are replaced with heated, moist flavored air having perhaps medication. The device requires a battery for heating purposes. U.S. Pat. No. 4,429,703 discloses a simulated cigarette which may be filled with an aromatic substance such as menthol to give a pleasant taste and smell. Such devices, however, may fail to provide an adequate psychological and physiological lift received either by the tobacco smoker or the user of cigarette substitutes offering nicotine, as described in U.S. Pat. No. 4,774,971. Considering that oxygen is a lift-providing substitute for tobacco, U.S. Pat. No. 3,631,856 outlines a simulated cigarette having a container of oxygen under pressure to provide a mixture of oxygen and a pleasant fragrance. The simulated cigarette disclosed in U.S. Pat. No. 4,184,496 allows a user, while simulating the action of smoking a cigarette or cigar, to circulate the air surrounding his nose and mouth which may be laden with actual cigarette or cigar smoke of others in the vicinity. The smokeless artificial cigarette outlined in U.S. Pat. No. 4,995,407 contains no tobacco and no nicotine, but utilizes beads or pellets emitting a stress-reducing vapor composed of at least one or more substances such as nutmeg oil, mace extract, neroli oil, valerian oil, myristicin, elemicin, and isoelemicin. Most of the beads are placed within the space in a tube containing a porous filler material, flavoring and aromatic substances, and two porous plugs which may include no or one or more beads. The act of oral inhalation through the tube provides a physiologically effective amount of vapor that produces a sense of satisfaction for the user. Patent Application Publication No. US 2002/0179101A1 also proposes a tubular body of material having a variety of taste and ingredients, but with no nicotine and tobacco, for suction by the user to receive psychological and physiological satisfaction, and thus reduce smoking. Air is drawn through a passage in the tubular material into the mouth of the user, thus simulating smoking.

Several patents on smokeless cigarettes have centered on controlled nicotine delivery. For example, the device disclosed under U.S. Pat. No. 4,393,884 enables a user to inhale pressurized nicotine or tobacco-like formulations on demand. The substance and the aerosol propellant such as nitrogen may be placed in the same or separate compartments, depending on the application. In contrast, the device under U.S. Pat. No. 4,284,089 offers the user vaporizable nicotine at room temperature and pressure without heating or burning tobacco. The device includes a constricted passageway formed by an absorbent material impregnated with a liquid nicotine mixture. The sucking action of the mouth increases air or gas velocity in the constricted passageway, resulting in a lower pressure suitable for enhanced vaporization of liquid nicotine. Clearly, the absorbent materials may also include volatile liquid ingredients to adjust the flavor for final nicotine vapor mixture. An improved version of this simulated smoking device, described by the same inventor under U.S. Pat. No. 4,813,437, utilizes fibrous materials for one or more nicotine bearing sections. To create some pressure drop for improving the release of nicotine-bearing vapors as air is drawn through the device, a primarily unobstructed insulating section is linearly arranged with a nicotine bearing section. To optimize the performance of cited devices, that is, to encourage the amount of nicotine that is uniformly vaporized without formation of unvaporized nicotine droplets, U.S. Pat. No. 4,793,366 discloses a device using microporous filament fibers for nicotine bearing. The cigarette-like device described in U.S. Pat. No. 6,041,789 is a relatively simple nicotine inhaler with air drawn in by the user. It consists of a long tube filled with porous polymeric material that has absorbed a solution of a volatile nicotinomimetic agonist in an amount effective for its released vapors to meet the physiological desires. The nicotine desire is addressed in U.S. Pat. No. 5,293,883 through the use of an array of small nicotine-containing ampules located within the mouth filter of the smokeless device. The simple device outlined under U.S. Pat. No. 5,284,163 also offers a smoke-free cigarette substitute that includes a tubular sleeve having a nicotine-containing carrier. However, nicotine is drawn into the oral cavity of the user through chewing. When pressure is applied to the filter liquid nicotine is released into the mouth of the user. This feature may be a disadvantage for some users as liquid nicotine has an extremely bitter, almost caustic taste. Patent Application Publication No. US2003/0111088A1 describes a tubular medication delivery device that supplies nicotine along with another drug in solution form. The mixture is essentially helpful for dispensing nicotine and naltrexone to manage patients who are smokers and also endure another addiction, such as alcoholism. In a previous disclosure under U.S. Patent Application No. 2002/0059939A1 the same inventor presented a similar device solely to deal with smoking cessation through nicotine treatment.

U.S. Pat. No. 5,293,883 also provides smell and sensation of a regular cigarette as air is drawn through two chambers containing unburned and pre-burned tobacco. This is also achieved in U.S. Pat. No. 4,892,109, but through an exothermic chemical reaction that heats air before its interaction with a charcoal, tobacco, or porous substrate including flavorant substances. The heated air carries tobacco flavor to the smoker's mouth without tobacco combustion. Patent Application Publication No. US 2005/0236006A1 describes several similar smoking and tobacco use cessation devices requiring no ignition and burning of substances. In one configuration, the device has two chambers, one for an exothermic reaction to heat the air before interaction in a second chamber with a source of tobacco, tobacco substitute, nicotine or nicotine substitute to cause evaporation. Further options include the delivery of substances such as vitamins, neutraceuticals, energy enhancers, aspirin, diet aids, weight loss additives, caffeine, breath enhancers and the like, for any desired effect. U.S. Pat. No. 4,911,181 offers several versions of a simulated smoking device through the use of mouthpiece that incorporates a plug of chewing tobacco or tobacco insert in a tube with a pumping component at its end or a tube with collapsible wall. Chewing or sucking creates a partial vacuum, resulting in the withdrawal of saliva from the user's mouth which interacts with tobacco for recirculation to the user's mouth. Commercial smokeless cigarettes have been introduced based on some of the concepts discussed above.

Nearly all smokeless cigarettes discussed above have the shape of a regular cigarette and provided the user with either a mixture of volatile agents, liquid substances, tobacco aromas, tobacco substitutes, or nicotine/nicotine substitutes as replacements for an all tobacco cigarette. None of these devices, however, addressed a key "smoking ritual": a constantly shifting grayish white stream that looks like or resembles cigarette smoke. Several methods, including chemical generation and aerosol formation have been attempted to reproduce cigarette smoke.

Several chemical-based approaches may be used to generate a white vapor, but their applications in a smokeless cigarette device are not practical due to several reasons such as size, cost, or possible heath restrictions. For example, normal liquefied gases may be used to produce fog, as in stage shows and concerts using a "fog machine". In contact with air these liquids generate copious amount of white vapors. The visible white trails are liquid water vapor condensed by the low temperature of the vapor evaporating from the liquid. Colder gas and damper location air produce superior fog. Liquid helium is a good choice because of its temperature of $-269°$ C., but it is very costly. Liquid nitrogen ($-196°$ C.) offers a large amount of white fog cloud, good cost-efficiency, and non-toxicity as the gas is present in air in large quantities (78%), but is not suitable for use in small locations. Liquid carbon dioxide ($-78°$ C.) and dry ice (solid $CO_2$ or solid carbon dioxide) offer a grey-white fog, but should not be handled in confined spaces as air containing more than 10% by volume of $CO_2$ is toxic. The normal concentration of $CO_2$ in air is less than a tenth of a percent. In addition, these liquids in contact with skin cause cold-burning, and thus are very dangerous in a liquid state. Boiling water from 100 to 200 degrees Celsius can generate a cloud-like fog, but such a vapor cannot be introduced into the mouth.

A water-based solution advertised as "fog juice" is often used in a "fog machine". All commercial fog machines require electrical power ranging from 400 to 1300 watts. According to one source, the fog is produced by heating the fog juice, which is a mixture of propylene glycol and triethylene glycol, mixed with 20 percent water. The fluid is directed into a narrow channel inside a heated metal block and is superheated before it is allowed to travel through a very small nozzle where the vaporized fog is expelled under high pressure. The nozzle and a protective cover become very hot during operation, and must not be placed near anything that may catch on fire. At high temperatures, the fog juice can decompose to harmful byproducts that may affect health. Similarly, mixing fumes from hydrochloric acid and ammonia (and also ammonium carbonate), as suggested in an early U.S. Pat. No. 726,037, forms a white cloud of ammonium chloride, but the approach is neither healthy nor environmentally green. Likewise, smoke generated from non-tobacco substances and other chemicals also produce health problems. A smokeless device in Patent Application Publication No. US 2005/0016553AI offers a two-chamber arrangement, with the first chamber providing an aroma evocative of the smell of flavor of burning tobacco or other fragrances. The aromatic compounds are deposited on a liner or are encapsulated in micro cells located within the first chamber. The aroma is released after the user scratches the liner or micro cells using, for example, a brush-like insert. The second chamber includes an amount of fine powder such as talc, or diatomaceous earth, which upon agitation, such as an ash flicking motion by the user, causes a small volume of the powder to flow through the device outlet aperture to simulate smoke. A check valve prevents powder particles from being sucked into the first chamber, thus not allowing them to enter the mouth of the user. A similar device may also have a tip that gives the appearance of glowing embers. Alternatively, a light emitting diode may be utilized with a red or orange light-transmitting plastic for the cap end.

Several devices have been suggested to deliver smoking flavor in the form of aerosol. A device in U.S. Pat. No. 4,765,347 delivers flavor via an aerosol generated by mechanical dispersion of a liquid into a flowing gas stream. The device consists of: 1) an outer container providing a pathway for airflow; and 2) an inner liquid container with a solution delivery tube placed at the center of a narrow aperture to cause air acceleration during puffing. This acceleration creates a region of lower pressure next to the output region of the solution delivery tube, relative to the pressure experienced by the liquid within the container, and is sufficient to draw a liquid column for dispersion as an aerosol into the mouth end region. Note that the flavor varies depending on the user. The volume of a puff of aerosol varies most generally from about 25 ml to about 35 ml during a puff period ranging from 1 to nearly 2.5 seconds. Alternatively, the flavor bed of tobacco or tobacco-derived material is often heated, without combustion of tobacco, to release tobacco flavors without producing all the normal products of tobacco combustion. As the smoker draws air through or around the heat source, the heated air releases tobacco flavors (vapor, aerosol or a mixture) into the smoker's mouth. Again, the heat source temperature is dependent on how the smoker uses the article, so that the flavor release rate varies widely from user to user. The device in U.S. Pat. No. 5,060,671 offers a cigarette-like arrangement to electrically heat a flavor source at a controlled temperature and for the uniformly release of the desired flavor with each puff, without overheating or burning. Microswitches sensitive to a change in pressure or air flow may be used to activate the device when the consumer draws the air. The heater is typically energized from about 0.1 second to about 4 seconds and for a temperature ranging from 100 C to about 600 C.

In addition to flavor, nicotine delivery has been achieved by means of an aerosol. A device in U.S. Pat. No. 4,945,929 includes nicotine and propellant storage containers linked to a nebulization nozzle to produce a nicotine spray. Large droplets in the conical aerosol are removed by impaction before the remaining aerosol pass through a series of baffles to increase evaporation time of the droplets, thus creating a mix which approximates that of tobacco smoke. Nicotine inhaler devices, based on ultrasonic nebulization, are found in U.S. Pat. Nos. 4,920,989 and 4,953,572. To stimulate either the upper respiratory tract or the lower respiratory tract or both, droplets must possess sizes ranging from 1 micron to about 10 microns in diameter. An inhaler was used in conjunction with nicotine patch as a method of aiding in the reduction of incidence of tobacco smoking. An aerosol of nicotine also was produced by an electronic cigarette described in Patent Application No. W02004080216. The device was non-flammable and offers no tar. An air flow sensor in the smoking-mouth of the cigarette delivered a signal to a circuit to start a high frequency vibrator receiving a nicotine solution from a container via a pipe, thus initiating aerosol formation by nebulization. The end cap in the front of the cigarette included cells and light diodes to give the appearance of a lighted cigarette. This device mimicked the usual smoking pattern and effect, giving the smokers the feel of smoking aside from nicotine delivery. An electronic cigar used a nebulization device. The "smoking liquid" for this device was a diluted nicotine fluid ready for nebulization in the inhaler container. The liquid was purified from tobacco according to the standard FDA GRAS, by biological technology, removing the harmful substances in the tobacco and keeping the safe or useful substances. As described, one ml of liquid was sufficient for about two packs of cigarettes. Another electronic cigar uses "supercritical atomizing technologies". A piezoelectric inhaler has been described, which includes an array of dispensing channels and an array of dispensing nozzles, to dispense droplets as an electric field applied to the channel walls. The field reduces the volume in an associated channel, creating a pressure pulse of flowable substance that lead to droplet formation. Because droplets per unit time can also be controlled, this approach offers a known volume of the substance sprayed.

A cigarette company that produces a "healthy" cigarette may lead the industry by selling the "novel smoke" at a considerable premium and capture market share from rivals.

Generally, needs exist for improved apparatus and methods for producing a cigarette with the appearance taste and other characteristics of a traditional cigarette with reduced adverse health consequences.

SUMMARY OF THE INVENTION

Embodiments of the present invention solve some of the problems and/or overcome many of the drawbacks and disadvantages of the prior art by providing an apparatus and method for producing an inhaler and/or artificial cigarette with the appearance and other characteristics of a traditional cigarette with reduced adverse health consequences. Other embodiments may most easily find use as artificial cigars, pipes or water pipes.

Certain embodiments of the invention accomplish this by providing a nebulizer apparatus including a housing, an air passage into the housing, a fog generator chamber within the housing connected to the air passage, a liquid source connected to the fog generating chamber, and a fog generator within the fog generating chamber for receiving liquid from the liquid source and creating an aerosol.

In embodiments of the present invention, the fog generator may be an ultrasonic nebulizer with the ultrasonic nebulizer including a piezoelectric surface on a flat transducer and a power supply for powering the ultrasonic nebulizer. One or more heat sinks may dissipate heat within the nebulizer apparatus.

In alternative embodiments of the present invention the fog generator may comprise a pneumatic nebulizer such as a glass frit with a means for creating a pressure differential across the pneumatic nebulizer, such as a venturi or a compressed air supply.

Embodiments of the present invention may include one or more air flow sensors for sensing movement of air through the air passage. The embodiments may also include a liquid valve disposed between the liquid source and the fog generating chamber controlled by the one or more air flow sensors, a compressed air supply for creating a pressure differential across the fog generator, the compressed air supply controlled by the one or more air flow sensors, and/or a power supply for powering the fog generator, the power supply controlled by the one or more air flow sensors.

Embodiments of the present invention may include a mouthpiece, a baffle for preventing large aerosol droplets from exiting the fog generating chamber, a fog chamber valve for closing the fog generating chamber during exhalation into the nebulizer apparatus, one or more aerosol exits connected to the air passage for directing exhaled air out of the nebulizer apparatus, and/or one or more valves for closing the one or more aerosol exits during inhalation and opening the one or more aerosol exits during exhalation.

In embodiments of the present invention, the liquid may be a pharmacological active agent.

Embodiments of the present invention may include a nebulizer method with steps including providing a nebulizer apparatus comprising a housing, an air passage into the housing, a fog generator chamber within the housing connected to the air passage, a liquid source connected to the fog generating chamber, and a fog generator within the fog generating chamber for receiving liquid from the liquid source and creating an aerosol, fluidly contacting the air passage with a user's mouth, inhaling through the nebulizer apparatus, and wherein the inhaling activates the fog generator.

Certain other embodiments of the invention can also be used in conjunction with the burning of tobacco or some other substance to increase the moisture level of the resulting smoke. For example, the nebulizer may be used in conjunction with a water pipe to deliver a more hydrated form of smoke to the user.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE PREFERRED EMBODIMENTS

Figure 1:
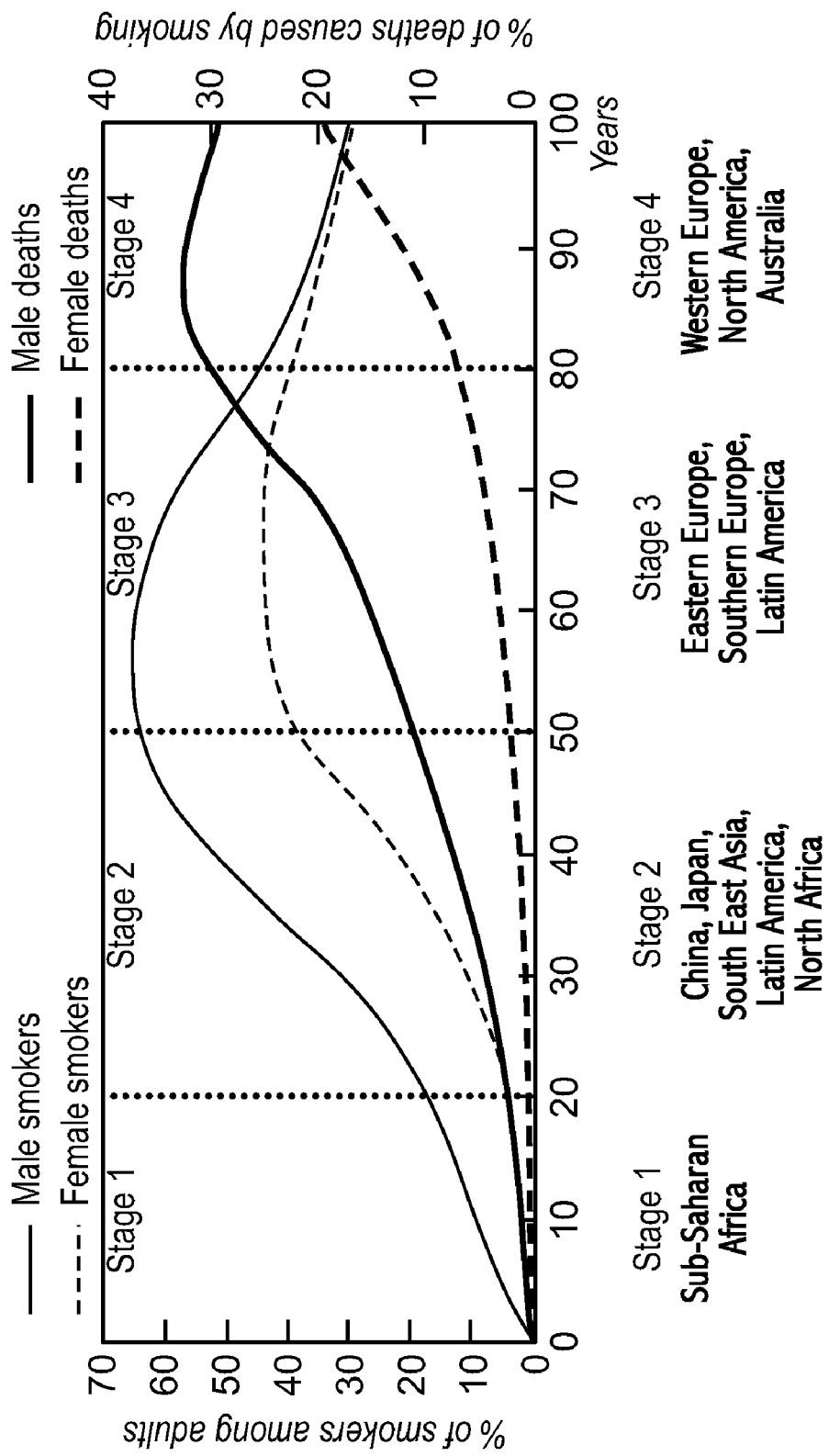
FIG. 1 is a graph showing stages of a worldwide tobacco epidemic.
Figure 2:
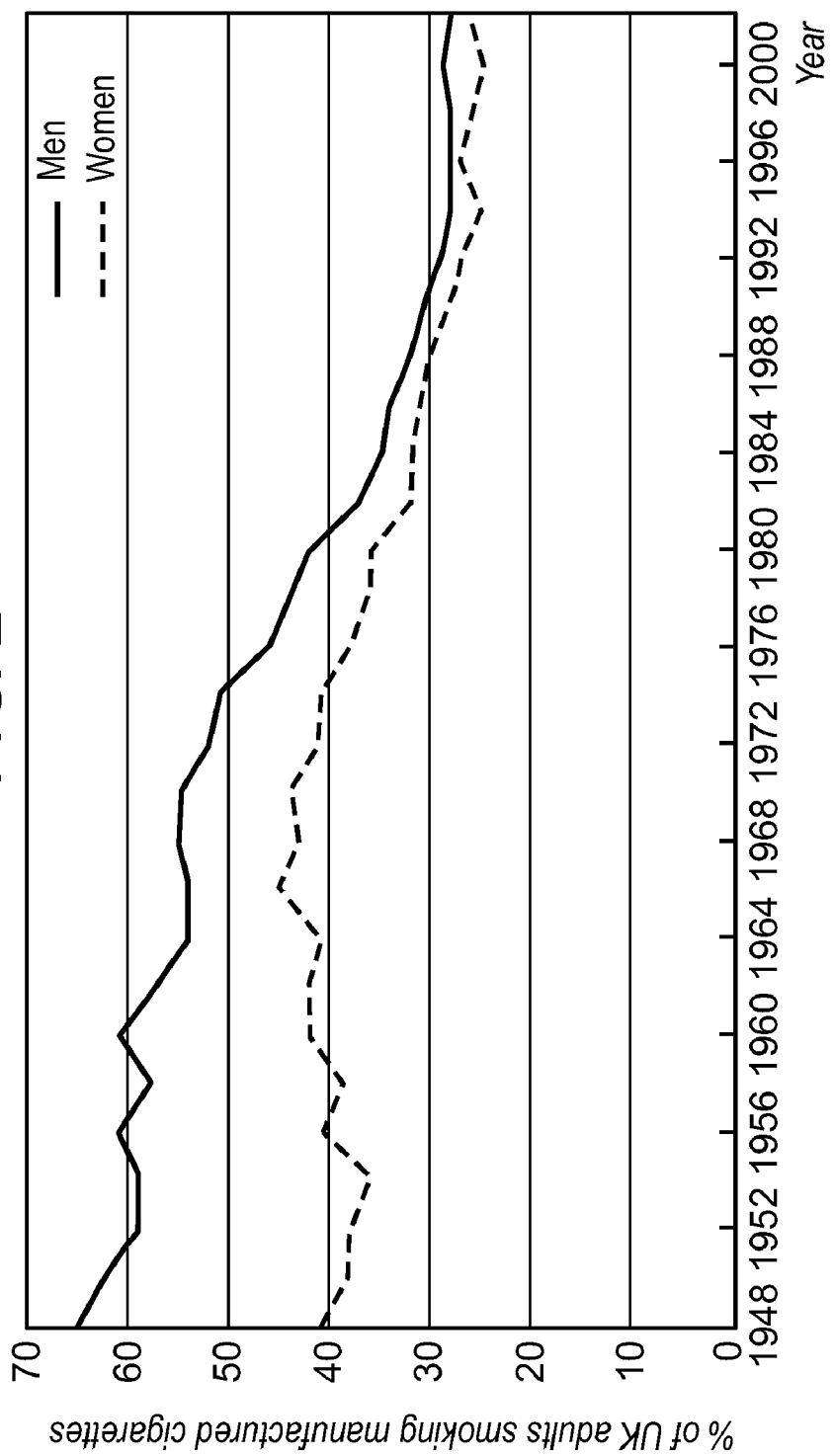
FIG. 2 is a graph showing the prevalence of smoking manufactured cigarettes in the United Kingdom.
Figure 3:
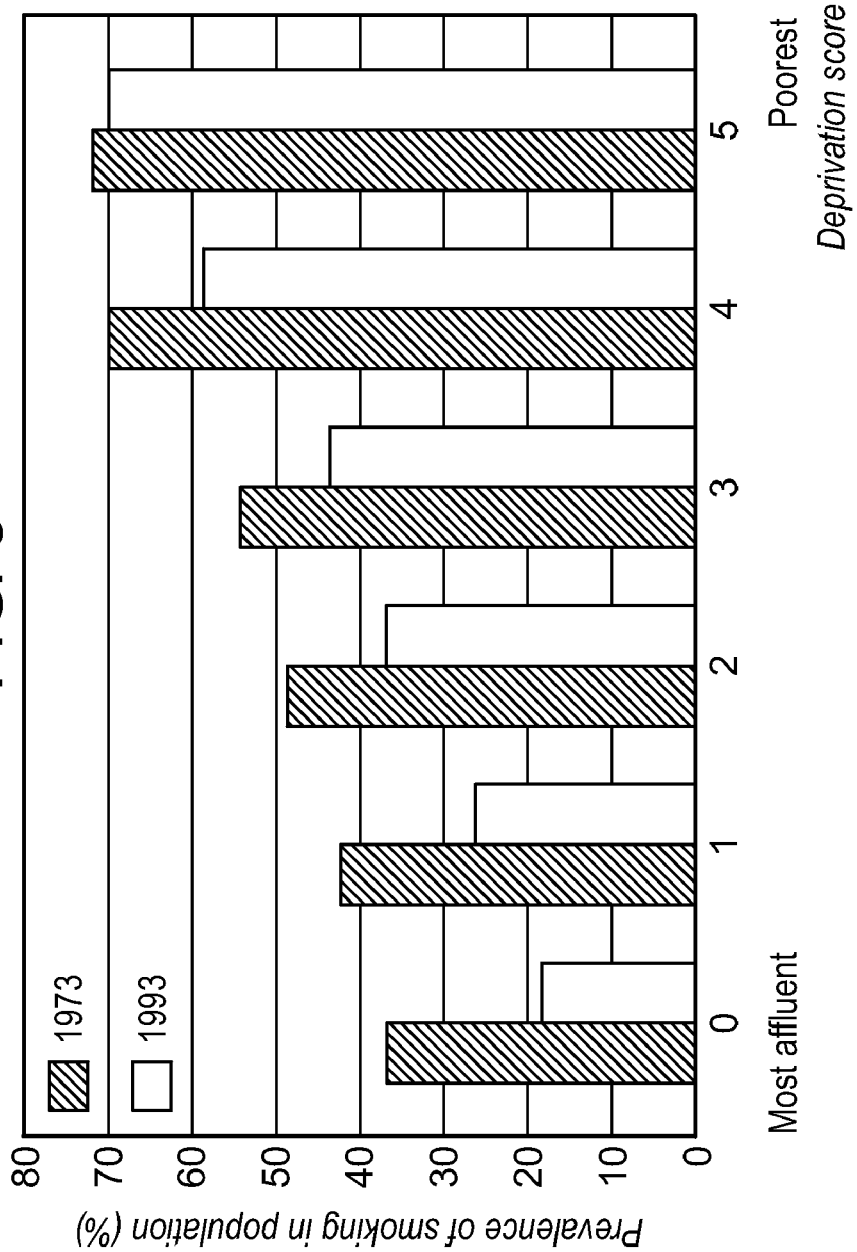
FIG. 3 is a graph showing cigarette smoking by deprivation level in the United Kingdom.
Figure 4:
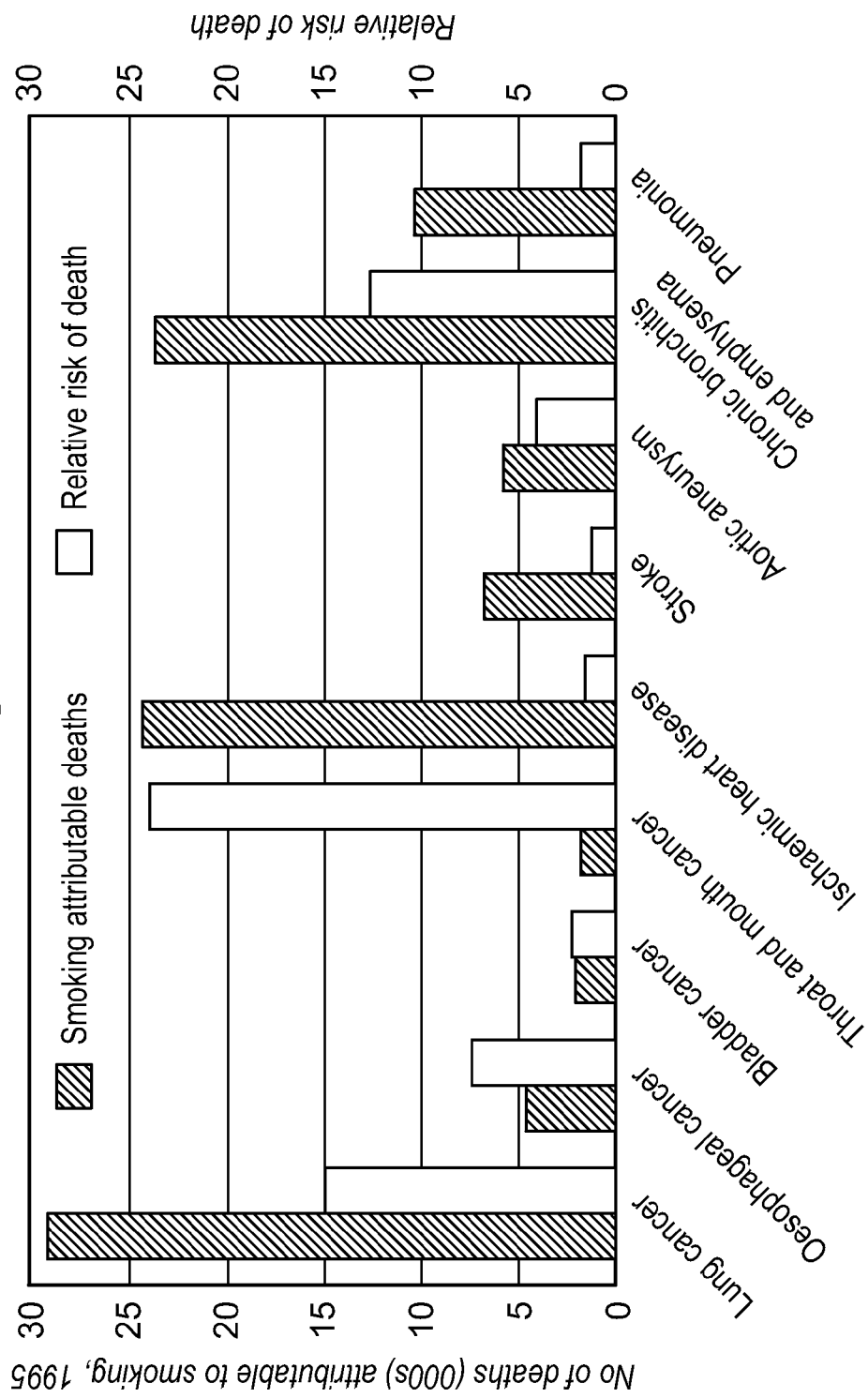
FIG. 4 is a graph showing numbers and relative risk of death by cause due to smoking in the United Kingdom.

Some preferred embodiments of the invention are discussed in detail below. While specific example embodiments may be discussed, it should be understood that this is done for illustration purposes only. A person skilled in the relevant art will recognize that other components and configurations may be used without patting from the spirit and scope of the invention.

Nearly all devices discussed in the Background of the Invention section above either did not produce an adequate smoking pattern and effect, or suffered from a list of problems outlined earlier. Embodiments of the present invention may involve generation of a visible vapor or fog via the production of aerosol from a liquid. Artificial cigarettes and/or inhalers with a visible vapor or fog may be generated by ultrasonically-activated flat crystals and/or pneumatic methods. Pneumatic methods may include crossflow and concentric nozzles, grid- and mesh-based approaches, and glass frit devices. Aerosols may be transported outside the artificial cigarette and/or inhalers via air, for example, by inhaling from the device, blowing into the devices and/or through exhalation.

While not wishing to be constrained by any specific theory, the inventor presently believes and others have suggested that in pneumatic nebulization with a concentric device, the liquid passes through a narrow tube encircled by a high-velocity gas flow parallel to a capillary axis. The liquid and gas streams reside at a perpendicular angle in a cross-flow device. Regardless of the device type, the flow of gas creates a pressure differential (P) across the liquid capillary, drawing the liquid into it at a liquid flow rate (Q) governed by Equation 1:

$$Q = \frac{R^4 P}{8 \eta L} \quad [1]$$

Note that the radius (R) and length (L) of the liquid capillary and the liquid viscosity ($\eta$) affect the liquid flow rate. For the formation of cloud-like smoke in the smokeless device, R should be reduced to limit the liquid requirement, and thus the device size. The gas flow necessary to create the differential pressure may be provided by the user through inhalation-exhalation or through a small pressurized container within the smokeless device.

Our present belief is that as the liquid, water or aqueous solution emerges from the capillary, it is shattered into an aerosol by the gas flow. The increase in relative gas velocity from approximately 5 to 50 m/s changes the liquid breakup pattern, thereby altering the size of droplets. In general, the droplet diameter is affected by liquid properties and nebulization device parameters as follows:

$$D_{3,2} = \frac{585}{V}\left[\frac{\sigma}{\rho_{liq}}\right]^{0.5} + 597\left[\frac{\eta_{liq}}{(\rho_{liq}\sigma)^{0.5}}\right]^{0.45}\left[\frac{10^3 Q_{liq}}{Q_{gas}}\right]^{1.5} \quad [2]$$

Equation 2 shows that the Sauter mean droplet diameter ($D_{3,2}$ in µm) is controlled by the difference between the gas and liquid velocities (V, m/s), the liquid surface tension ($\sigma$, dyn/cm), the liquid density ($\rho_{liq}$, g/cm$^3$) the liquid viscosity ($\eta_{liq}$, poises), and the volume flow rates of the liquid and gas ($Q_{liq}$ and $Q_{gas}$, respectively, cm³/s). For the smokeless device under our consideration, adjustments of three parameters (V, $Q_{liq}$ and $Q_{gas}$) change the droplet size distribution and thus the fog density. For practical reasons, it is preferred to use 2 CC or 2 ML as the maximum volume of liquid suitable for the intended device when it is in the form of a cigarette. In a device of the form of a cigar, normal pipe or water pipe, this volume can be increased; however, most embodiments of the invention are designed to have maximal aerosol production efficiency with minimal liquid consumption.

To increase fog density, ultrasonic energy may be used. In contrast to pneumatic nebulization ultrasonic nebulization is independent of gas flow. In ultrasonic nebulization, the liquid may be delivered onto or already resides on the surface of a piezoelectric transducer driven by an ultrasonic generator at a frequency of approximately 200 kHz to 10 MHz. The ultrasonic waves travel vertically from the crystal surface towards the liquid-air interface. The resulting oscillation may shatter the surface liquid, i.e., the liquid film, into an aerosol under certain conditions. The amplitude of the wave must be adequately large to upset the liquid film on the surface of the piezoelectric crystal, leading to droplet formations. Importantly, the mean numerical diameter of droplets (or average droplet diameter, D) is controlled by the surface wave wavelength (λ), and is expressed by:

$$D = 0.34\lambda \quad [3]$$

$$\lambda = \left(\frac{8\pi\sigma}{\rho f^3}\right)^{\chi} \quad [4]$$

where f is the ultrasonic frequency. The average droplet diameter is affected also by the surface tension (σ) and the liquid density.

A key issue is the volume of liquid in a container of the smokeless device for aerosol generation. For practical reasons, certain embodiments of the present invention consider 2 CC or 2 mL as the maximum volume. Other maximum volumes are possible. It is preferred to have maximal aerosol production efficiency with minimal liquid consumption. For ultrasonic devices according to the present invention, the efficiency of aerosol production may be approximately 10 to 20 times higher than certain pneumatic methods.

There are several forms of ultrasonic devices. In one type, a transducer may be bonded to a chemically-resistant plate and placed vertically in a horizontal spray chamber. In another type, a transmitting bath may be used to transfer ultrasonic radiation from a transducer to a liquid to be nebulized.

Figure 5:
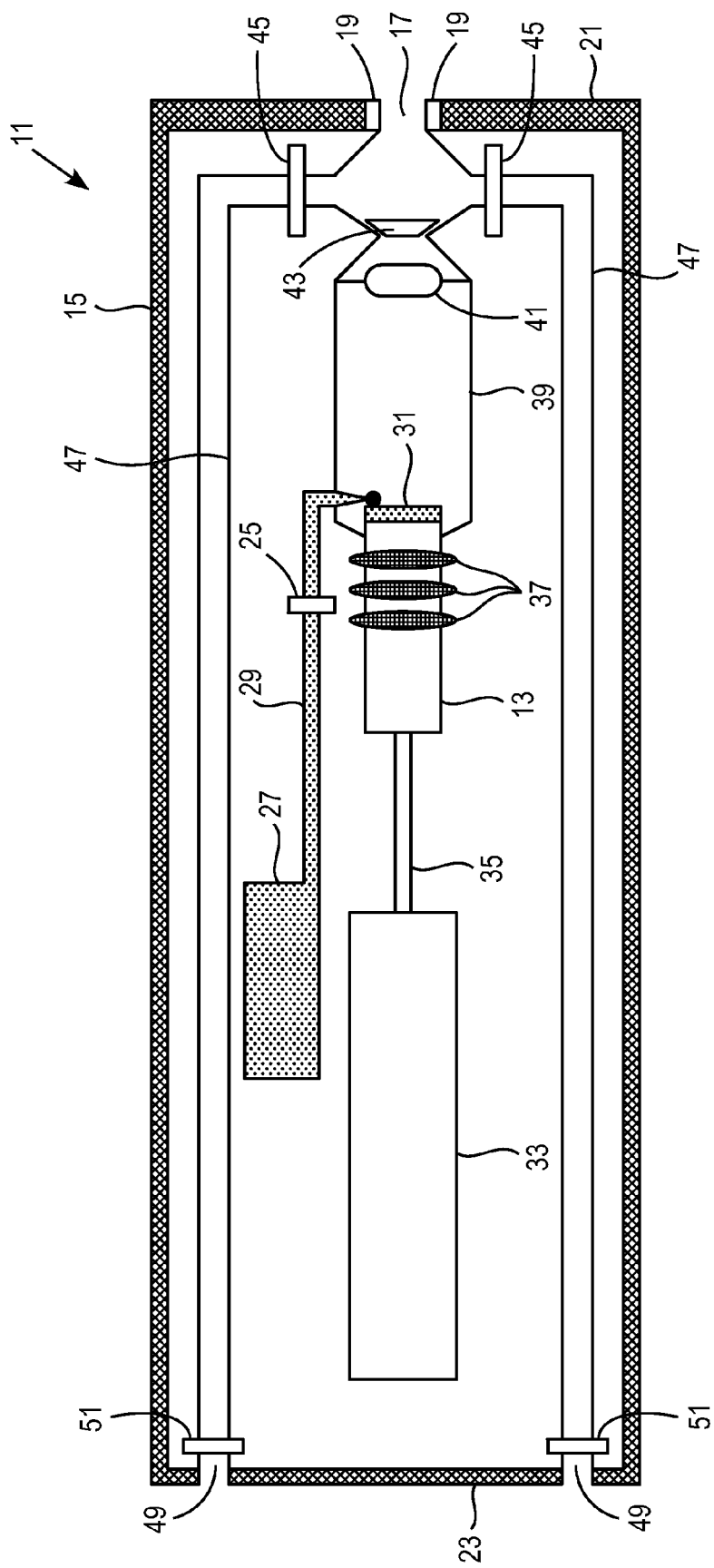
FIG. 5 is a schematic cross section of an artificial cigarette with a flat transducer for applications in fog generation for the artificial cigarette.

FIG. 5 shows an artificial cigarette 11 with a flat transducer 13 for applications in fog generation for the artificial cigarette 11. The artificial cigarette 11 may be any shape or size, but is preferably shaped and sized to resemble a traditional cigarette. A housing 15 may enclose the artificial cigarette 11. The housing 15 may have a first end 21 proximate to a user's mouth and a second end 23 distal to a user's mouth. An aerosol passageway 17 may lead from the inside of the artificial cigarette 11 into a user's mouth. One or more air flow sensors 19 may surround the aerosol passageway 17 or may be found in a location suitable to determine the presence of airflow into and out of a user's mouth. Fog may be generated in response to the movement of air past the one or more air flow sensors 19.

A user may place the artificial cigarette 11 into the user's mouth and inhale through the artificial cigarette 11 in a manner similar to a traditional cigarette. Upon detection of inhalation, the one or more air flow sensors 19 may transmit a signal to a liquid valve 25 located within the housing 15. The liquid valve 25 may open to allow liquid from a storage tank 27 to pass from the storage tank 27, through a carrier tube 29, past the liquid valve 25 and onto a piezoelectric surface 31. The storage tank 27 is preferably a 2 mL storage tank, but may be other sizes to accommodate different uses of the invention. A 2 mL storage tank 27 may be sufficiently small with a sufficient volume of liquid for applications of the artificial cigarette 11. The liquid may be water, a water-based solution, or another chemical that produces sufficient aerosol fog per volume of liquid.

The detection of inhalation by the one or more air flow sensors 19 may also activate a power supply 33. Different air flow sensors 19 may control the operation of the liquid valve 25 and the power supply 33. The power supply 33 is preferably a disposable battery-based power source. The power supply 33 may be connected to the flat transducer 13 by an input 35. The input is preferably a radio frequency input to the flat transducer 13. The flat transducer 13 may generate fog through ultrasonic nebulization. One or more heat sinks 37 may be disposed around the flat transducer 13 for dissipating heat generated within the artificial cigarette 11. The piezoelectric surface 31 may be located at an end of the flat transducer 13.

The piezoelectric surface 31 may extend or may be located within a fog generation chamber 39. Liquid from the storage tank 27 may contact the piezoelectric surface 31. The power supply 33 powers the flat transducer 13 and causes the piezoelectric surface 31 to vibrate ultrasonically. The ultrasonic vibrations create an aerosol of the liquid within the fog generation chamber 39. As air is drawn into a user's mouth, a vacuum is created within the artificial cigarette 11. Air and the created aerosol are drawn out of the fog generation chamber 39 and towards the user's mouth. A baffle 41 at the exit of the fog generation chamber 39 prevents larger droplets of liquid from exiting the fog generation chamber 39 and entering the user's mouth. Any excess liquid remaining in the fog generation chamber 39 may be directed to a second container (not shown) for subsequent use through a similar scheme or may be recycled to the storage tank 27. Smaller aerosol droplets pass the baffle 41, a fog chamber valve 43, and the aerosol passageway 17 before entering the user's mouth. The cessation of inhalation may be detected by the one or more airflow sensors 19 and signals are sent to close the liquid valve 25 and turn off the power source 33. The passage of the aerosol droplets into the user's mouth completes the inhalation stage of the operation of the artificial cigarette. During inhalation, one or more flap valves 45 remain closed. The flap valves 45 are held closed by the negative pressure of the inhalation.

A user may then exhale through the artificial cigarette 11. If a user exhales through the artificial cigarette 11, some of the aerosol that entered the user's mouth may pass back through the artificial cigarette 11. The one or more air flow sensors 19 may detect the exhalation. The air pressure of the exhalation may close the fog chamber valve 43 to prevent the exhaled air from entering the fog generation chamber 39. The one or more flap valves 45 may open to allow exhaled air to pass through one or more aerosol exit passages 47 and out of the artificial cigarette 11 through one or more aerosol exits 49. The one or more flap valves are preferably located proximate to the aerosol passageway 17. A second set of one or more flap valves 51 may be located proximate to the one or more aerosol exits 49.

The inhalation and exhalation process may be repeated until the storage tank 27 no longer contains any liquid.

Embodiments are also contemplated that permit the recharging of the liquid storage tank. The artificial cigarette 11 may operate through inhalation and puffing, without any additional input by the user.

Figure 6:
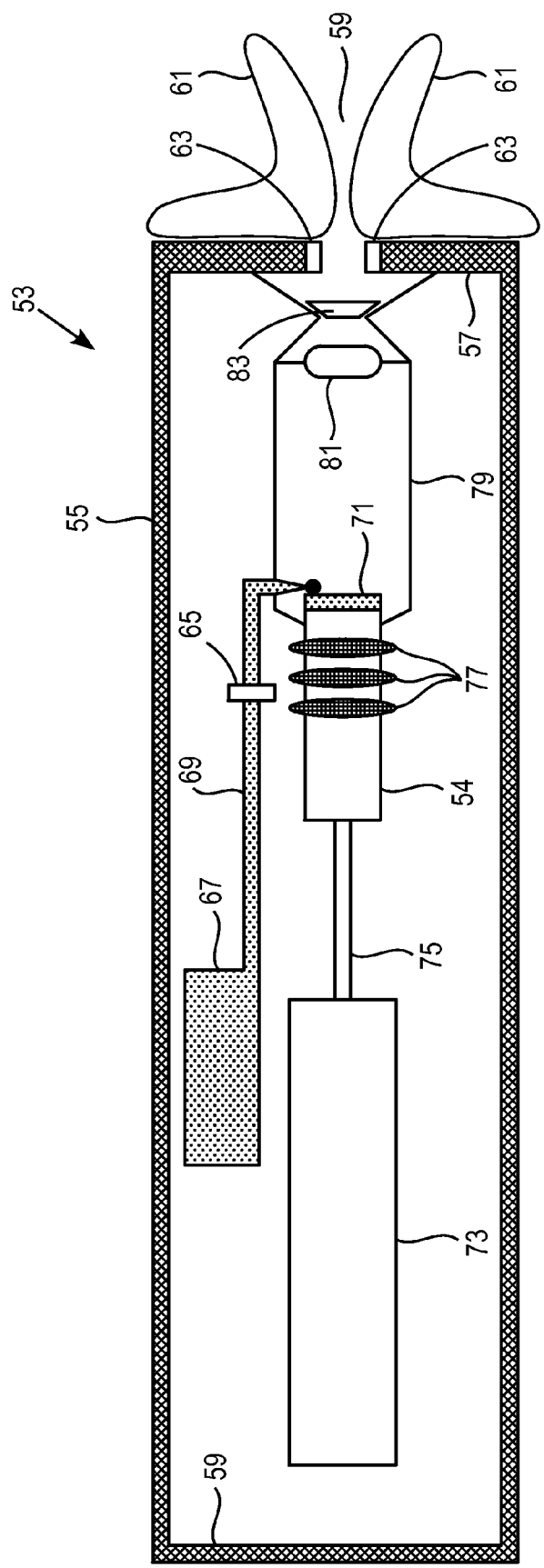
FIG. 6 is a schematic cross section of an inhaler with a flat transducer for applications in fog generation for the inhaler.

FIG. 6 shows an inhaler 53 with a flat transducer 54 for applications in fog generation for the inhaler 53. The inhaler 53 may be any shape or size, but is preferably shaped and sized for portability and to resemble a traditional inhaler. A housing 55 may enclose the inhaler 53. The housing 55 may have a first end 57 proximate to a user's mouth and a second end 59 distal to a user's mouth. An aerosol passageway 59 may lead from the inside of the inhaler 53 into a user's mouth. A mouth piece 61 may facilitate use of the inhaler 53 and direction of the aerosols into the user's mouth. One or more air flow sensors 63 may surround the aerosol passageway 59 or may be found in a location suitable to determine the presence of airflow into and out of a user's mouth. Fog may be generated in response to the movement of air past the one or more air flow sensors 63.

A user may place the mouthpiece 61 into or against the user's mouth and in a manner similar to traditional inhalers. Upon detection of inhalation, the one or more air flow sensors 63 may transmit a signal to a liquid valve 65 located within the housing 55. The liquid valve 65 may open to allow liquid from a storage tank 67 to pass from the storage tank 67, through a liquid carrier tube 69, past the liquid valve 65 and onto a piezoelectric surface 71. The storage tank 67 is preferably a 2 mL storage tank but may be other sizes to accommodate different uses of the invention. A 2 mL storage tank 67 may be sufficiently small with a sufficient volume of liquid for applications of the inhaler 53. The liquid may be water, a water-based solution, asthma medication, other pharmaceuticals, or another chemical that produces sufficient aerosol fog per volume of liquid.

The detection of inhalation by the one or more air flow sensors 63 may also activate a power supply 73. Different air flow sensors 63 may control the operation of the liquid valve 65 and the power supply 73. The power supply 73 may be a battery-based power source or a dynamo based power source. The power supply 73 may be connected to the flat transducer 54 by an input 75. The input is preferably a radio frequency input to the flat transducer 54. The flat transducer 54 may generate fog through ultrasonic nebulization. One or more heat sinks 77 may be disposed around the flat transducer 54 for dissipating heat generated within the inhaler 53. The piezoelectric surface 71 may be located at an end of the flat transducer 54.

The piezoelectric surface 71 may extend or may be located within a fog generation chamber 79. Liquid from the storage tank 67 may contact the piezoelectric surface 71. The power supply 73 powers the flat transducer 54 and causes the piezoelectric surface 71 to vibrate ultrasonically. The ultrasonic vibrations create an aerosol of the liquid within the fog generation chamber 79. As air is drawn into a user's mouth, a vacuum is created within the inhaler 53. Air and the created aerosol are drawn out of the fog generation chamber 79 and towards the user's mouth. A baffle 81 at the exit of the fog generation chamber 79 prevents larger droplets of liquid from exiting the fog generation chamber 79 and entering the user's mouth. Any excess liquid remaining in the fog generation chamber 79 may be directed to a second container (not shown) for subsequent use through a similar scheme or may be recycled to the storage tank 67. Smaller aerosol droplets pass the baffle 81, a fog chamber valve 83, and the aerosol passageway 59 before entering the user's mouth. The passage of the aerosol droplets into the user's mouth completes the delivery phase of the inhaler 53. The cessation of inhalation may be detected by the one or more airflow sensors 63 and signals are sent to close the liquid valve 65 and turn off the power source 73.

The inhalation process may be repeated until the storage tank 67 no longer contains any liquid. Embodiments are also contemplated that permit the recharging of the liquid storage tank. The inhaler may operate through inhalation without any additional input by the user.

Alternative embodiments of the present invention may be based upon pneumatic production of aerosols. Two basic configurations for pneumatic production of mist or white cloud may be used: concentric type and crossflow type. In both arrangements, a pressure differential may be formed across a capillary. The pressure differential may move a liquid through the capillary and may form an aerosol with no need for electrical power.

Concentric type pneumatic production of aerosols may allow operation at a low liquid flow rate (approximately 1-100 µL/min) and low gas flow rate (approximately 0.15 L/min) with good aerosol formation efficiency. The intensity of the fog may be useful as an artificial cigarette and/or as an inhaler or delivery of medicaments.

Crossflow type pneumatic production of aerosols may allow water to emerge from a top of a V-type slot having a small hole. The emerging water may form a thin water film Gas may be directed through the hole, rupturing the water film and producing an aerosol. To enhance mist production and reduce water consumption, artificial cigarettes and/or inhalers may include two parallel grids spaced approximately 2 mm apart. A first grid may be wet by the water, which is blown off the grid. The second grid may be used for pulse dampening and further breakup of the water droplets. A notch around a perimeter of a first grid may transfer a consistent liquid film onto the surface of the first grid. A gas nozzle behind the first grid may deliver gas to the first grid, which produces aerosol upon contact with the liquid. Impaction of the aerosol on a second grid may further fragment the aerosol, generating smaller and more uniform droplets with higher efficiency. A grid-based pneumatic production may offer improved aerosol production stability.

Alternative embodiments of the present invention may be based around three basic types of porous glass frit: (1) a flat plate, (2) a cylindrical frit pressurized externally, and (3) a thimble-shaped frit pressurized internally. For a flat plate device, air may be directed from the back section of the frit with water introduced on a front side of the disk to create an aerosol. In a cylindrical glass frit device, water may be directed onto the inside surface of a frit cylinder while air may be applied externally on the fritted cylinder. In a thimble-shaped frit device, water may be applied onto an outside surface of a thimble frit to form a thin liquid film with air introduced internally to pass through the pores of the frit and break a liquid film into the mist or fog. The flat frit may use a porous glass (with pore sizes of approximately 4 to 8 micrometer) for nebulizing the water. The analyte transport efficiency may approach 94% at 5 to 50 microliter/minute when the aerosol mean droplet diameter is approximately 0.1 µm. Depending on the frit pore size, air flow rate can be as low as 20 mL/min. A pore size of approximately 1-1.6 micrometers may be used for the thimble glass frit to increase the velocity of gas through the pores, thereby producing a more efficient nebulizer.

Figure 7A:
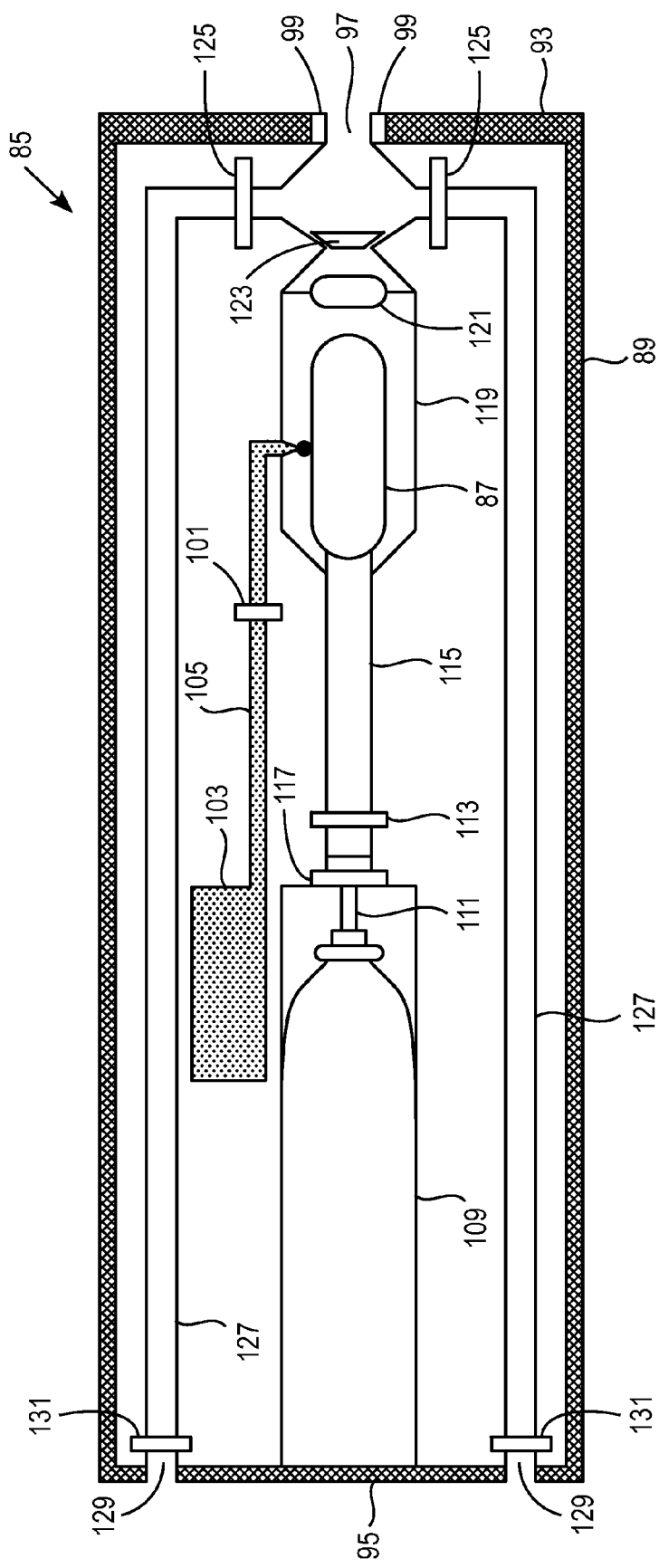
FIG. 7A is a schematic cross section of an artificial cigarette using a thimble frit.
Figure 7B:
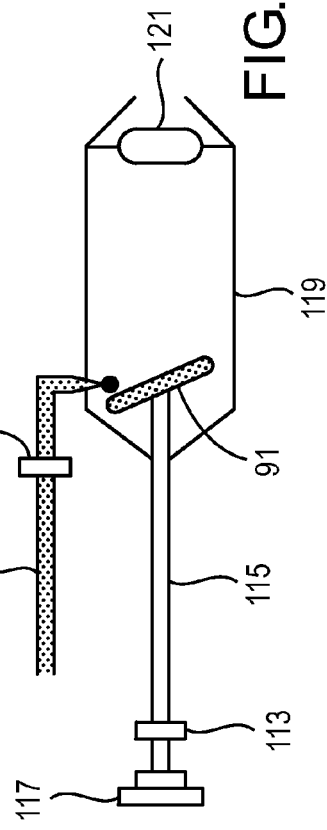
FIG. 7B is a schematic cross section of an artificial cigarette using a flat glass frit.

FIG. 7A shows an artificial cigarette 85 using a thimble frit 87. FIG. 7B shows a detail of an artificial cigarette 85 using a flat glass frit 91. Other types of frits are possible. The artificial cigarette 85 may be any shape or size, but is preferably shaped and sized to resemble a traditional cigarette. A housing 89 may enclose the artificial cigarette 85. The housing 89 may have a first end 93 proximate to a user's mouth and a second end 95 distal to a user's mouth. An aerosol passageway 97 may lead from the inside of the artificial cigarette 85 into a user's mouth. One or more air flow sensors 99 may surround the aerosol passageway 97 or may be found in a location suitable to determine the presence of airflow into and out of a user's mouth. Fog may be generated in response to the movement of air past the one or more air flow sensors 99.

A user may place the artificial cigarette 85 into the user's mouth and inhale through the artificial cigarette 85 in a manner similar to a traditional cigarette. Upon detection of inhalation, the one or more air flow sensors 99 may transmit a signal to a liquid valve 101 located within the housing 85. The liquid valve 101 may open to allow liquid from a storage tank 103 to pass from the storage tank 103, through a carrier tube 105, past the liquid valve 101 and onto the thimble frit 87 or flat glass frit 91. The storage tank 103 is preferably a 2 mL storage tank, but may be other sizes to accommodate different uses of the invention. A 2 mL storage tank 103 may be sufficiently small with a sufficient volume of liquid for applications of the artificial cigarette 85. The liquid may be water, a water-based solution, or another chemical that produces sufficient aerosol fog per volume of liquid.

The detection of inhalation by the one or more air flow sensors 99 may also activate a compressed air supply 109 via a compressed air valve 113. Different air flow sensors 99 may control the operation of the liquid valve 101 and the compressed air valve 113. The compressed air supply 109 is preferably a canister-type device with a nozzle 111 extending from an end of the compressed air supply 109. The nozzle 111 of the compressed air supply 109 may be connected to the thimble frit 87 or the flat glass frit 91 by a compressed air passageway 115. Upon detection of inhalation, the compressed air valve 113 may be released, allowing compressed air to pass from the compressed air supply 109, through the nozzle, through a connector for compressed air 117, through the compressed air valve 113, through the compressed air passageway 115 and onto the thimble frit 87 or the flat glass frit 91. The connector for compressed air 117 may connect the nozzle 111 to the compressed air valve 113. The thimble frit 87 or the flat glass frit 91 may generate fog through pneumatic production.

The thimble frit 87 or the flat glass frit 91 may be located within a fog generation chamber 119. Liquid from the storage tank 103 may contact the thimble frit 87 or the flat glass frit 91. The compressed air supply 109 creates air pressure through the thimble frit 87 or the flat glass frit 91 as described above, creating an aerosol of the liquid within the fog generation chamber 119. As air is drawn into a user's mouth, a vacuum is created within the artificial cigarette 85. Air and the created aerosol are drawn out of the fog generation chamber 119 and towards the user's mouth. A baffle 121 at the exit of the fog generation chamber 119 prevents larger droplets of liquid from exiting the fog generation chamber 119 and entering the user's mouth. Any excess liquid remaining in the fog generation chamber 119 may be directed to a second container (not shown) for subsequent use through a similar scheme or may be recycled to the storage tank 103. Smaller aerosol droplets pass the baffle 121, a fog chamber valve 123, and the aerosol passageway 97 before entering the user's mouth. The cessation of inhalation may be detected by the one or more airflow sensors 99 and signals are sent to close the liquid valve 101 and turn off the compressed air source 109. The passage of the aerosol droplets into the user's mouth completes the inhalation stage of the operation of the artificial cigarette 85. During inhalation, one or more flap valves 125
remain closed. The flap valves 125 are held closed by the negative pressure of the inhalation.

A user may then exhale through the artificial cigarette 85. If a user exhales through the artificial cigarette 85, some of the aerosol that entered the user's mouth may pass back through the artificial cigarette 85. The one or more air flow sensors 99 may detect the exhalation. The air pressure of the exhalation may close the fog chamber valve 123 to prevent the exhaled air from entering the fog generation chamber 119. The one or more flap valves 125 may open to allow exhaled air to pass through one or more aerosol exit passages 127 and out of the artificial cigarette 85 through one or more aerosol exits 129. The one or more flap valves are preferably located proximate to the aerosol passageway 97. A second set of one or more flap valves 131 may be located proximate to the one or more aerosol exits 129.

The inhalation and exhalation process may be repeated until the storage tank 103 no longer contains any liquid. Embodiments permitting recharging of the storage tanks are also contemplated. The artificial cigarette 85 may operate through inhalation and puffing, without any additional input by the user.

Figure 8:
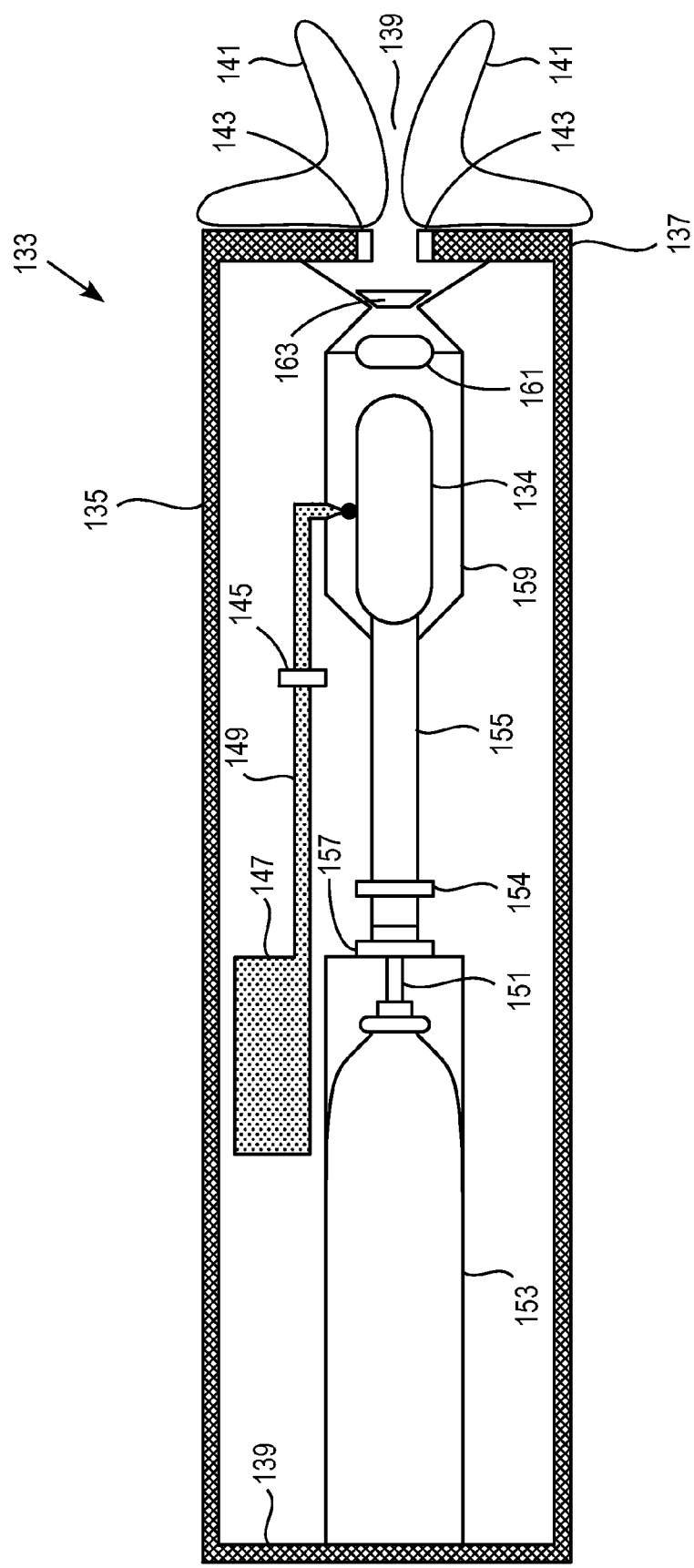
FIG. 8 is a schematic cross section of an inhaler using a thimble frit.

FIG. 8 shows an inhaler 133 using a thimble frit 134. Other types of frits are possible. The inhaler 133 may be any shape or size, but is preferably shaped and sized for portability and to resemble a traditional inhaler. A housing 135 may enclose the inhaler 133. The housing 135 may have a first end 137 proximate to a user's mouth and a second end 139 distal to a user's mouth. An aerosol passageway 139 may lead from the inside of the inhaler 133 into a user's mouth. A mouth piece 141 may facilitate use of the inhaler 133 and direction of the aerosols into the user's mouth. One or more air flow sensors 143 may surround the aerosol passageway 139 or may be found in a location suitable to determine the presence of airflow into and out of a user's mouth. Fog may be generated in response to the movement of air past the one or more air flow sensors 143.

A user may place the mouthpiece 141 into or against the user's mouth and in a manner similar to traditional inhalers. Upon detection of inhalation, the one or more air flow sensors 143 may transmit a signal to a liquid valve 145 located within the housing 135. The liquid valve 145 may open to allow liquid from a storage tank 147 to pass from the storage tank 147, through a liquid carrier tube 149, past the liquid valve 145 and onto the thimble frit 134. The storage tank 147 is preferably a 2 mL storage tank, but may be other sizes to accommodate different uses of the invention. A 2 mL storage tank 147 may be sufficiently small with a sufficient volume of liquid for applications of the inhaler 133. The liquid may be water, a water-based solution, asthma medication, other pharmaceuticals, or another chemical that produces sufficient aerosol fog per volume of liquid.

The detection of inhalation by the one or more air flow sensors 143 may also activate a compressed air supply 153. Different air flow sensors 143 may control the operation of the liquid valve 145 and the compressed air supply 153. The compressed air supply 153 is preferably a canister-type device with a nozzle 151 extending from an end of the compressed air supply 153. The nozzle 151 of the compressed air supply 153 may be connected to the thimble frit 134 by a compressed air passageway 155. Upon detection of inhalation, a compressed air valve 154 may be released, allowing compressed air to pass from the compressed air supply 153, through the nozzle 151, through a connector for compressed air 157, through the compressed air valve 153, through the compressed air passageway 155 and onto the thimble frit 134. The connector for compressed air 157 may connect the nozzle 151 to the compressed air valve 154. The thimble frit 134 may generate fog through pneumatic production.

The thimble frit 134 may be located within a fog generation chamber 159. Liquid from the storage tank 147 may contact the thimble frit 134. The compressed air supply 153 creates air pressure through the thimble frit 134 as described above, creating an aerosol of the liquid within the fog generation chamber 159. As air is drawn into a user's mouth, a vacuum is created within the inhaler 133. Air and the created aerosol are drawn out of the fog generation chamber 159 and towards the user's mouth. A baffle 161 at the exit of the fog generation chamber 159 prevents larger droplets of liquid from exiting the fog generation chamber 159 and entering the user's mouth. Any excess liquid remaining in the fog generation chamber 159 may be directed to a second container (not shown) for subsequent use through a similar scheme or may be recycled to the storage tank 103. Smaller aerosol droplets pass the baffle 161, a fog chamber valve 163, and the aerosol passageway 139 before entering the user's mouth. The passage of the aerosol droplets into the user's mouth completes the delivery phase of the inhaler 133. The cessation of inhalation may be detected by the one or more airflow sensors 143 and signals are sent to close the liquid valve 145 and turn off the compressed air source 153.

The inhalation process may be repeated until the storage tank 103 no longer contains any liquid. Embodiments permitting recharging of the storage tank could easily be engineered. The inhaler 133 may operate through inhalation without any additional input by the user.

The artificial cigarette and inhaler devices of the present invention may provide for inhalation and/or exhalation of substances other than liquid aerosol. Additional substances may be contained within the liquid, such as fragrances, nicotine, pharmaceuticals, etc. The additional substances may enhance the use of the artificial cigarette or inhaler and provide medical treatment of assistance in the cessation of smoking.

Alternative fog generations schemes are contemplated for embodiments of the present invention. An alternative artificial cigarette or inhaler may be based on piezoelectric ink-jet nozzles for dispensing and vaporizing precisely known amounts of water solution as droplets. Yet another artificial cigarette or inhaler may be based on a thermospray through introduction of water into a heated capillary. In a thermospray device liquid may begin to boil near the outlet of the capillary and may be converted to an aerosol or a mist by the expanding solution vapor. The artificial cigarette or inhaler may offer aerosols with fine droplets. Furthermore, electrical devices provide a white cloud or fog and are generally powered, for example, by a small, disposable battery.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A nebulizer apparatus comprising:

a housing with a distal end and a proximal end, a fog generating chamber within the housing, an aerosol passageway fluidly connecting the proximal end of the housing with the fog generating chamber, a fog chamber valve regulating flow of gas between the aerosol passageway and the fog generating chamber, a liquid source in fluid communication with the fog generating chamber, and a fog generator within the fog generating chamber for receiving liquid from the liquid source and creating an aerosol.

2. The apparatus of claim 1, wherein the fog generator is an ultrasonic nebulizer.

3. The apparatus of claim 2, wherein the ultrasonic nebulizer comprises a piezoelectric surface on a flat transducer.

4. The apparatus of claim 2, further comprising a power supply for powering the ultrasonic nebulizer.

5. The apparatus of claim 4, further comprising one or more heat sinks for dissipating heat within the nebulizer apparatus.

6. The apparatus of claim 1, wherein the fog generator is a pneumatic nebulizer.

7. The apparatus of claim 6, wherein the pneumatic nebulizer is a glass frit.

8. The apparatus of claim 6, further comprising a compressed air supply for creating a pressure differential across the pneumatic nebulizer.

9. The apparatus of claim 1, further comprising one or more air flow sensors for sensing movement of air through the air passage.

10. The apparatus of claim 9, further comprising a liquid valve disposed between the liquid source and the fog generating chamber controlled by the one or more air flow sensors.

11. The apparatus of claim 9, further comprising a compressed air supply for creating a pressure differential across the fog generator, the compressed air supply controlled by the one or more air flow sensors.

12. The apparatus of claim 9, further comprising a power supply for powering the fog generator, the power supply controlled by the one or more air flow sensors.

13. The apparatus of claim 1, further comprising a mouthpiece.

14. The apparatus of claim 1, further comprising a baffle for preventing large aerosol droplets from exiting the fog generating chamber.

15. The apparatus of claim 1, wherein the fog chamber valve closes the fog generating chamber during exhalation into the nebulizer apparatus.

16. The apparatus of claim 1, further comprising one or more aerosol exits connected to the air passage for directing exhaled air out of the nebulizer apparatus.

17. The apparatus of claim 16, further comprising one or more aerosol exit valves for closing the one or more aerosol exits during inhalation and opening the one or more aerosol exits during exhalation.

18. The apparatus of claim 1, wherein the liquid comprises a pharmacological active agent.

19. An artificial cigarette apparatus comprising:

a housing with a proximal end and a distal end, a fog generating chamber within the housing, a liquid source in fluid communication with the fog generating chamber, a fog generator within the fog generating chamber for receiving liquid from the liquid source and creating an aerosol, a baffle for preventing large aerosol droplets from exiting the fog generating chamber, an aerosol passageway fluidly connecting the proximal end of the housing with the fog generating chamber, a fog chamber valve regulating flow of gas between the aerosol passageway and the fog generating chamber, and for closing the fog generating chamber during exhalation into the nebulizer apparatus, one or more aerosol exits in fluid communication with the aerosol passageway for directing exhaled air out of the nebulizer apparatus, and one or more aerosol exit valves for closing the one or more aerosol exits during inhalation and opening the one or more aerosol exits during exhalation.

20. The apparatus of claim 19, wherein the fog generator is a piezoelectric surface on a flat transducer.

21. The apparatus of claim 19, wherein the fog generator is a glass frit.

* * * * *